US007811988B2

(12) United States Patent
Johansson et al.

(10) Patent No.: US 7,811,988 B2
(45) Date of Patent: Oct. 12, 2010

(54) LIPID MIXTURES FOR SYNTHETIC SURFACTANTS

(75) Inventors: Jan Johansson, Parma (IT); Tore Curstedt, Parma (IT); Bengt Robertson, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 907 days.

(21) Appl. No.: 10/558,563

(22) PCT Filed: May 26, 2004

(86) PCT No.: PCT/EP2004/005683

§ 371 (c)(1),
(2), (4) Date: Dec. 26, 2006

(87) PCT Pub. No.: WO2004/105726

PCT Pub. Date: Dec. 9, 2004

(65) Prior Publication Data

US 2008/0045449 A1  Feb. 21, 2008

(30) Foreign Application Priority Data

May 30, 2003  (EP) .................................. 03012417

(51) Int. Cl.
*A61K 31/23* (2006.01)
(52) U.S. Cl. ............................................ 514/7; 514/12
(58) Field of Classification Search ........................ None
See application file for complete search history.

(56) References Cited

U.S. PATENT DOCUMENTS

| 5,653,996 A * | 8/1997 | Hsu ........................... 424/450 |
| 7,053,044 B1 * | 5/2006 | Curstedt et al. ................ 514/2 |
| 7,511,011 B2 * | 3/2009 | Curstedt et al. ................ 514/2 |
| 2002/0072540 A1 | 6/2002 | Larsson et al. |
| 2003/0091509 A1 | 5/2003 | Haefner et al. |

FOREIGN PATENT DOCUMENTS

| WO | WO 00/47623 | * | 8/2000 |
| WO | 02/06301 | | 1/2002 |

OTHER PUBLICATIONS

Palmblad, J. of Biochem., 1999, vol. 338, pp. 381-386.*
Darfler, Frederick J. et al.,"Preparation and Use of Lipid Microemulsions As Nutritional Supplements for Culturing Mammalian Cells", in Vitro Cellular & Developmental Biology, vol. 26, No. 8, pp. 779-783, 1990.

* cited by examiner

*Primary Examiner*—Christopher R. Tate
*Assistant Examiner*—Roy Teller
(74) *Attorney, Agent, or Firm*—Oblon, Spivak, McClelland, Maier & Neustadt, L.L.P.

(57) ABSTRACT

The present invention provides novel lipid mixtures for synthetic surfactants. In particular, the invention provides a specific lipid mixture containing a specific amount of polyunsaturated phospholipids to be used for the preparation of synthetic surfactants. Said surfactants and pharmaceutical compositions thereof are useful for the treatment of surfactant deficiencies like respiratory distress syndrome (RDS).

25 Claims, No Drawings

LIPID MIXTURES FOR SYNTHETIC SURFACTANTS

BACKGROUND OF THE INVENTION

Endogenous pulmonary surfactant reduces surface tension at the air-liquid interface of the alveolar lining, preventing the lungs from collapsing at end expiration. Surfactant deficiency is a common disorder in premature infants and causes respiratory distress syndrome (RDS), which can be effectively treated with preparations which are lipid extracts of minced mammalian lung or lung lavage. Said preparations are known as modified natural surfactants and they are mainly composed of phospholipids (PLs) such as phosphatidylcholine (PC), phosphatidylethanolamine (PE) and phosphatidylglycerol (PG) and the hydrophobic surfactant proteins B and C (SP-B and SP-C).

For clarity, a list of PLs cited in this patent application follows:
phosphatidylcholine: PC,
phosphatidylethanolamine: PE,
phosphatidylglycerol: PG,
phosphatidylinositol: PI,
phosphatidylserine: PS,
sphingomyelin: SM,
1,2-dipalmitoyl-sn-glycero-3-phosphoglycerol, generally known as dipalmitoyl-phosphatidylglycerol: DPPG,
1,2-dipalmitoyl-sn-glycero-3-phosphocholine, generally known as dipalmitoyl-phosphatidylcholine: DPPC,
1-palmitoyl-2-oleyl-sn-glycero-3-phosphoglycerol, generally known as palmitoyl-oleyl-phosphatidylglycerol: POPG,
1-palmitoyl-2-oleyl-sn-glycero-3-phosphocholine generally known as palmitoyl-oleyl-phosphatidylcholine: POPC,
1,2-dioleyl-sn-glycero-3-phosphoglycerol generally known as dioleyl-phosphatidylglycerol: DOPG,
1-palmitoyl-2-linoleyl-sn-glycero-3-phosphocholine, generally known as palmitoyl-linoleyl-phosphatidylcholine: PLPC,
1-stearoyl-2-arachidonoyl-sn-glycero-3-phosphocholine, generally known as stearoyl-arachidonoyl-phosphocholine (SAPC),
1-palmitoyl-2-arachidonoyl-sn-glycero-3-phosphocholine (PAPC),
1,2-dipalmitoyl-sn-glycero-3-phosphoethanolamine, generally known as dipalmitoyl-phosphatidylethanolamine: DPPE,
1,2-distearoyl-sn-glycero-3-phosphoethanolamine, generally known as distearoyl-phosphatidylethanolamine: DSPE,
1,2-dipalmitoyl-sn-glycero-3-phospho-L-serine, generally known as dipalmitoyl-phosphatidylserine: DPPS.

The glycerol moieties of the phospholipids are mainly esterified with long chain fatty acids ($C_{14}$-$C_{20}$) which in turn can be saturated (e.g. myristic, palmitic and stearic acid), monounsaturated (e.g. oleic acid) or polyunsaturated (e.g. linoleic and arachidonic acid).

Phospholipids containing as the characterizing residues neutral or zwitter-ionic moieties such as glycerol (PG), inositol (PI) and serine (PS) are known as acidic phospholipids. Other examples of acidic phospholipids are DPPG, POPG and DPPS.

Surfactants are usually administered to premature infants in the form of aqueous suspensions by instillation into the lungs through the trachea. They can also be administered to adults affected by various pathologies involving a severe pulmonary insufficiency such as adult respiratory distress syndrome (ARDS).

In order to have optimal properties from a bio-physical and pharmacological/therapeutic standpoint, a surfactant preparation should: i) effectively lower the surface tension; ii) have a good spreading rate; iii) have a low viscosity in order to allow the preparation of a concentrated suspension in an aqueous medium with optimal delivery and distribution properties at alveolar level, upon administration in a small volume by intratracheal instillation.

The capability of the surfactants of lowering the surface tension as well as other parameters such as the spreading rate can be tested in vitro using several methods, for example the "captive bubble method" as described in Schurch, S., Bachofen, H. Goerke, J., Possmayer, H. (1989) "A captive bubble method reproduces the in situ behaviour of lung surfactant monolayers" *J. Appl. Physiol.*, 67: 2389-2396.

One of the most important lipidic components of surfactant preparations is 1,2-dipalmitoyl-sn-glycero-3-phosphocholine (DPPC) as it forms a monomolecular film at the air-liquid interface during compression, probably undergoing phase transition (solidification) during surface compression, thereby stabilizing a system of alveoli with different sizes.

It is also generally recognized that acidic phospholipids are of paramount importance in order to obtain a good activity since they favour the spreading of DPPC.

On the other hand, high concentrations of a saturated PL such as DPPC can affect other properties of the lipid suspension, such as the viscosity of the preparation.

The possibility of preparing concentrated suspension in a small volume is a feature of particular importance for the administration of surfactants to low-weight newborns by endotracheal instillation.

The modified natural surfactants available for therapeutic use, have a concentration generally comprised between 25 and 50 mg/ml. Only one of them, "Curosurf®", is available at a higher concentration, that is 80 mg/ml.

Surfactant preparations obtained from animal tissues present anyway some drawbacks, like their availability in limited amounts, the complexity of the production and sterilization processes and the relevant production costs: as a consequence, many efforts have been made to prepare synthetic surfactants.

According to Wilson (Expert Opin Pharmacother 2001, 2, 1479-1493), synthetic surfactants are distinguished in:

"artificial" surfactants devoid of surfactant proteins, simply consisting of mixtures of synthetic compounds, primarily phospholipids and other lipids that are formulated to mimic the lipid composition and behaviour of natural surfactant; and "reconstituted" surfactants which are artificial surfactants to which have been added surfactant proteins isolated from animals or manufactured through recombinant technology such as those described in WO 95/32992, or synthetic surfactant protein analogues such as those described in WO 89/06657, WO 92/22315 and WO 00/47623.

The development of reconstituted surfactants has to a large extent been focused on the surfactant protein analogues while the lipid composition has obtained less attention.

Not much information about the composition and lipid mixture concentration of synthetic surfactants under development is available.

In a phase III, pivotal, masked, multinational, randomized trial, 5.8 ml/kg or 175 mg/kg of Surfaxin® were administered for comparing its properties vs Exosurf® in preventing RDS (Moya F. et al Abstract n. 2643 of the Annual Meeting of the Paediatric Academy Societies, San Francisco, May 1-4, 2004). From these values it can be extrapolated that Surfaxin® was administered at a concentration of 30 mg/ml.

Surfaxin®, also reported as KL4-Surfactant is a synthetic peptide-containing surfactant prepared by mixing the phospholipids dipalmitoyl-sn-glycero-3-phosphocholine (DPPC) and 1-palmitoyl-2-oleoyl-sn-glycero-3-phosphoglycerol (POPG) in a 3:1 ratio by weight with palmitic acid (PA), 15% by weight compared with the phospholipids, in an organic solvent.

In a previous study it was also utilized at two concentrations: 26.6 mg/ml and 35 mg/ml, expressed as phospholipid concentration (*Am J Respir Crit Care Med* 1996, vol 153, pp 404-410).

PRIOR ART

In the prior art, data about the lipid composition of artificial and/or reconstituted surfactants have been reported in the following documents.

Suzuki et al (Eur J Respir Dis 1986, 69, 336-345) described the in vitro and in vivo properties of a surfactant made of low-molecular weight surfactant proteins and phospholipid mixture constituted of DPPC and 1,2-dipalmitoyl-sn-glycero-3-phosphoglycerol (DPPG) in the ratio 80:20 by weight. Although they have reported that unsaturated phospholipids promote effective spreading at air-liquid interface, DPPG was found superior to unsaturated PG in a system of DPPC recombined with a small apoprotein.

In Notter et al (Clin Perinatology 1987, 14, 433-479) the effects of lipids or phospholipids such as dioleyl-PC, PE, cholesterol, short-chain saturated-PC, fatty acids and glycerides on the re-spreading properties of DPPC have been reviewed. The general results have been of an enhanced dynamic respreading compared to DPPC alone. In the text it is also reported that artificial surfactants made of DPPC:egg-PG 7:3 have been used in the literature.

In Darfler F J (In Vitro Cell Dev Biol. 1990, 26(8), 779-83) protein-free lipid microemulsions suitable for use in tissue culture are prepared from purified, synthetic lipids to produce a homogeneous, water-soluble, stable suspension that can be sterile-filtered. The composition of the microemulsion was optimised observing the effects on chinese hamster ovary (CHO) cells growth. The prepared microemulsions reported in Table 2 contain alpha-tocopherol and at least 16.3% of cholesterol acetate.

WO 89/06657 and WO 92/22315 in the name of Scripps are directed to polypeptide analogous of SP-B, Although in the specification it is generically reported that the lipid portion (of the surfactant compositions, editor's note) is preferably about 50 to about 90, more preferably about 50 to 75, weight percent DPPC with the remainder unsaturated PC, PG, triacylglycerols, palmitic acid, sphingomyelin or a mixture thereof, nevertheless in the examples of both applications, samples of surfactants containing 4 or 10 mg/ml of a mixture of DPPC:PG 3:1 (75:25) by weight were assessed for their in vitro properties. For studying the in vivo properties, a concentration of 20 mg/ml of the same mixture was used, in some cases further containing palmitic acid.

In Cochrane et al (Science, 1991, 254, 566-568), the behaviour in vitro of simplified peptides such as $KL_4$ and PL made of DPPC and PG 3:1, DPPC and 1-palmitoyl-2-oleyl PG (POPG) 3:1, DPPC and 1-palmitoyl-2-oleyl-PC (POPC) 3:1 has been investigated. $KL_4$ was tested at a concentration of 3% while the others peptides at concentration of 3-5%. The in vivo properties of 3% $KL_4$ in a lipid mixture of DPPC:POPG (a monounsaturated phospholipid) in 3:1 ratio and 15% palmitic acid was also tested. The authors generically conclude that the combination of these simplified peptides and DPPC:POPG provide excellent surfactant in 27 day-old fetal rabbits and 130 day-old fetal rhesus monkeys.

In Yu et al (Biochimica and Biophysica Acta 1992, 1126, 26-34), the pulsating bubble technique was used to study the surface activity of binary phospholipids mixture containing DPPC and unsaturated acidic PLs such as egg-PG, POPG or egg-phosphatidic acid in the ratio 7:3 w/w in combination with 1% SP-B.

In the patent application WO 95/32992 in the name of Byk Gulden directed to polypeptides analogues of SP-C, it is generically reported that the phospholipid portion could comprise DPPC, POPG (or PG) and a salt such as Ca or Mg or Na chloride to reduce viscosity. In the examples, a mixture of DPPC:POPG:palmitic acid 7:3:0.25+$CaCl_2$ has been utilised.

Curstedt et al (9$^{th}$ International Workshop on Surfactant Replacement, Jerusalem, May 22-25, 1994) reported on the in vitro activity of SP—C analogous recombined with the following lipid mixtures: DPPC:POPC:DOPG 55:35:10, wherein POPC and DOPG are monounsaturated phospholipids; DPPC:PG 7:3; DPPC:PG:palmitic acid 68:22:9, with or without $CaCl_2$. The preparation containing DPPC:PG:palmitic acid 68:22:9 had a faster adsorption rate and a lower equilibrium surface tension than the other lipid mixtures.

Krill et al (*Chemistry and Physics of Lipids* 71, 47-59, 1994) reached the same conclusions; in a study aimed at evaluating the in vitro properties of surfactant compositions made of a synthetic protein B fragment, DPPC and POPG, they suggested that the presence of palmitic acid helps in establishing a stable lipid film of DPPC, capable of achieving low surface tension values. No indication of the ratio among the components is reported.

In WO 00/47623 in the name of the applicant, directed to SP-C analogue peptides, it is generically reported that suitable lipids/phospholipids may be selected from the group consisting of PC (preferably DPPC), PG, palmitic acid, triacylglycerols, sphingomyelin. In the examples, surfactant preparations made of one of the claimed peptides, e.g. SP-C (LKS) in combination with DPPC:PG 7:3 w/w or DPPC:PG:palmitic acid 68:22:9 w/w/w have been tested in vitro.

In Palmblad et al (Biochem J 1999, 339, 381-386), the same data of WO 00/47623 were reported. In the paper, it is also stated that optimal in vitro characteristics were obtained from a preparation containing SP-C(LKS), SP-B, DPPC and PG, i.e. when palmitic acid was omitted from the lipid mixture.

Diemel et al (J Biol Chem, 2002, 277, 21179-21188) reported on the structural properties of surfactant mixtures made of SP-B and DPPC:DPPG 80:20 or DPPC:POPG 80:20 or DPPC:POPC:DPPG 60:20:20.

In the latter mixture, saturated (DPPG) and monounsaturated (POPC) phosholipid were used.

WO 02/06301 refers to a method of treating conditions associated with lipid oxidation or microbial proliferation and includes the step of administering a composition comprising a pharmacologically effective amount of an antioxidant or antimicrobial lung surfactant protein compound such as proteins A and D and derivatives thereof. In the text it is generically stated that methods in accordance with the invention comprise administering said compounds in combination with a carrier which may be an organic solvent, phosphatidylcholine, cholesterol or surfactant phosholipids. In the examples a surfactant lipid mixture, composed of egg phosphatidylcholine, dipalmitoylphosphatidylcholine (DPPC), cholesterol and 1-oleoyl-2-linoleoyl-sn-glycero-3 phosphocholine (1:1: 0.15:0.15, w/w, respectively) was used as a substrate to check the capability of lung surfactant proteins of preventing lipid oxidation. In this mixture, egg-PC and DPPC, are present in amounts of 43%, while 1-oleoyl-2-linoleoyl-sn-glycero-3 phosphocholine and cholesterol are present in an amount of 7%, respectively on the total weight of the mixture. The mixture does not contain acidic phopsholipids.

US 2002/0072540 is directed to a lung surfactant composition comprising a lung surfactant, which-when dispersed as powder or particles in 0.9% w/w sodium chloride in a concentration of 10% w/w at ambient temperature-is capable of forming, in the course of swelling, a birefringent network or tubules at an air-liquid-solid interface within a time period of from about 0.5 min to about 120 minutes as observed by polarising microscopy. In the text it is generically stated that a lung surfactant composition according to the invention comprises phospholipids such as, e.g. saturated and unsaturated phospholipids or mixtures thereof. The phospholipids may comprise dipalmityl phosphatidylcholine (DPPC).

Evans et al (Lipids 15, 524-535) report that surface viscosities of most of the fully saturated phospholipids are very high and those of certain unsaturated ones is very low. They also report that cholesterol reduce surface viscosities in monolayers of DPPC. However they do not teach how to adjust the composition of the lipid mixture of a surfactant preparation in order to reduce its viscosity while maintaining the capacity of effectively reducing low surface tension during film compression.

In most of the documents of the prior art concerning lipid mixtures as vehicles for lung surfactants, lipid compositions comprising a content of saturated PLs, and in particular, DPPC equal to or higher than 70% by weight in combination with PG or POPG have been utilized or suggested as preferable in particular for decreasing surface tension to low values.

However, a relatively high content of saturated PLs may affect rheological properties by increasing the viscosity of the preparation, in particular when a concentrated synthetic surfactant composition, i.e. equal to or higher than about 30 mg/ml, preferably higher than 40 mg/ml, more preferably higher than 50 mg/ml, is desired. A high viscosity indeed can negatively affect the spreading of the surfactant and hence its distribution into the broncho-alveolar part of the lungs (King et al *Am J Physiol Lung Cell Mol Physiol* 2002, 282, L277-L284). Moreover, in order to prepare concentrated suspensions of lipid mixtures comprising high contents of saturated PLs with an acceptable viscosity, it is necessary to resort to procedures of heating and vigorous stirring.

In view of these drawbacks, it would be highly advantageous to provide lipid mixtures to be used in the preparation of synthetic surfactants which, while allowing to achieve good in vitro and in vivo properties, are able to keep low the viscosity of concentrated surfactant preparations favouring their delivery and distribution into the broncho-alveolar part of the lungs upon administration.

SUMMARY OF THE INVENTION

The present invention is directed to a lipid mixture for preparing a synthetic surfactant consisting of at least 95% by weight of phospholipids, said phospholipids comprising:

1,2-dipalmitoyl-sn-glycero-3-phosphocholine (DPPC) in an amount of at least 40% by weight, preferably comprised between 40% and 65% by weight, more preferably comprised between 45% and 60% and in particular comprised between 45% and 55% by weight;

polyunsaturated phospholipids in an amount higher than 10% by weight, preferably higher than 20% by weight, more preferably comprised between 20% and 45% by weight and in particular between 30% and 40% by weight; and saturated or monounsaturated acidic phospholipids in an amount higher than 10% by weight, preferably comprised between 10% and 30% by weight more preferably comprised 15% and 30% by weight, all the amounts being calculated on the total weight of the lipid mixture;

optionally further comprising a neutral lipid in an amount up to 5% by weight.

It has indeed been found that by using a lipid mixture with such a composition it is possible to prepare surfactant preparations characterised by good in vitro properties, i.e. low surface tension and fast spreading rate during film compression as well as good biological activity. In vivo experiments carried out in immature newborn rabbits have indeed proved that reconstituted surfactants containing one of the lipid mixture of the invention give rise to high tidal volumes and Lung Gas Volumes values.

In particular, it has been found that reconstituted surfactants containing an amount of unsaturated PLs higher than 30% and of acidic phospholipids higher than 10% give rise to better performances in terms of Lung Gas Volumes values than those containing a lower amount.

The synthetic surfactant preparations containing the lipid mixtures of the invention have technological characteristics which allow the preparation of concentrated aqueous suspension, equal to or higher than 30 mg/ml, preferably higher than 40 mg/ml, more preferably higher than 50 mg/ml up to 80 mg/ml of phospholipid mixture, characterized by a low viscosity, advantageously comprised between 5 and 20 centipoise and preferably between 6 and 15 centipoise, so favouring their delivery and distribution to the lungs upon administration.

DETAILED DESCRIPTION OF THE INVENTION

The characteristics of the lipid mixtures of the invention and the corresponding synthetic surfactant preparations will be described in the following detailed description.

Advantageously the lipid mixture consists of at least 95% of phospholipids by weight, preferably at least 98%, by weight. The phospholipid fraction contains 1,2-dipalmitoyl-sn-glycero-3-phosphocholine (DPPC) in an amount of at least 40% by weight, preferably comprised between 40% and 65% by weight, more preferably comprised between 45% and 60% and in particular comprised between 45% and 55% by weight calculated on the total weight of the lipid mixture.

DPPC can be either prepared by synthetic route or obtained from a natural source.

Advantageously the phospholipid fraction contains an amount of polyunsaturated phospholipids higher than 10% by weight, preferably higher than 20% by weight, more preferably comprised between 20% and 45% by weight and in particular between 30% and 40% by weight, calculated on the total weight of the lipid mixture.

As polyunsaturated phospholipids we intend phospholipids (PL) as defined before, in which at least one of the esterifying fatty acid residues contains more than one double bond in the aliphatic chain. Typical polyunsaturated fatty acid residues are linoleic acid, linolenic acid and arachidonic acid. Polyunsaturated phospholipids of this kind are phosphatidylcholine (PC), phosphatidylinositol (PI), phosphatidylethanolamine (PE), phosphatidylserine (PS), phosphatidylglycerol (PG) and sphingomyelin (SM).

Preferred polyunsaturated phospholipids are 1-palmitoyl-2-linoleyl-sn-glycero-3-phosphocholine (PLPC), 1-palmitoyl-2-arachidonoyl-sn-glycero-3-phosphocholine (PAPC) and 1-stearoyl-2-arachidonoyl-sn-glycero-3-phosphocholine (SAPC).

The polyunsaturated phospholipids are generally commercially available and can be either prepared by synthetic route or obtained from a natural source, for example from mammalian tissues.

In one embodiment of the invention, as a source of polyunsaturated phospholipids, natural extracts can also be used. For example, phosphatidylethanolamines isolated from egg (egg-PE) or a phospholipid mixture containing polyunsaturated fatty acids obtained by isolation from liver (liver-PL) can also be used. Egg-PE contains different esterifying acids and, among others, the polyunsaturated linoleic and arachidonic acids. The liver-PL has usually an average percent composition of about PC 50%, PE 25%, sphingomyelin 10%, acidic phospholipids 15% by weight wherein some of the PL species are esterified with polyunsaturated acids. The person skilled in the art shall use the egg-PE and/or the liver-PL in such an amount that the final composition of the lipid mixture fulfils the requirements of the lipid mixture of the invention.

Advantageously the phospholipid fraction contains saturated or monounsaturated acidic phospholipids in an amount higher than 10% by weight, preferably comprised between 10% and 30% by weight, more preferably comprised 15% and 30% by weight, calculated on the total weight of the lipid mixture.

As saturated acidic phospholipids we intend phospholipids such as phosphatidylglycerol, phosphatidylinositol, phosphatidylserine wherein the esterifying fatty acids are saturated while for monounsaturated acidic phospholipids we intend those wherein at least one of the esterifying fatty acids is monounsaturated. Typical examples of saturated PLs are 1,2-dipalmitoyl-sn-glycero-3-phosphoglycerol (DPPG) and 1,2-dioleyl-sn-glycero-3-phosphoglycerol (DOPG) and 1,2-dipalmitoyl-sn-glycero-3-phospho-L-serine (DPPS). Examples of monounsaturated PLs are 1-palmitoyl-2-oleyl-sn-glycero-3-phosphoglycerol (POPG) and 1-palmitoyl-2-oleyl-sn-glycero-3-phosphocholine (POPC). Preferably, the acidic phospolipids in the lipid mixture of the invention will be 1,2-dipalmitoyl-sn-glycero-3-phosphoglycerol (DPPG), 1-palmitoyl-2-oleyl-sn-glycero-3-phosphoglycerol (POPG) and their mixtures.

Besides DPPC, polyunsaturated phospholipids and saturated or monounsaturated acidic phosholipids, the phospholipid fraction of the lipid mixture of the invention can contain other phospholipids wherein the esterifying fatty acids are saturated or monounsaturated. Typical phospholipids of said class are 1,2-dipalmitoyl-sn-glycero-3-phosphoethanolamine (DPPE) are 1,2-distearoyl-sn-glycero-3-phosphoethanolamine (DSPE).

Advantageously, in the lipid mixture of the invention, the ratio between saturated and unsaturated (monounsaturated and polyunsaturated) phospholipids will be comprised between 65:35 and 40:60 by weight, preferably between 55:45 and 45:55 by weight and the ratio between the acidic phospholipids and the other phospholipids will be comprised between 10:90 and 30:70 by weight, preferably between 15:85 and 25:75 by weight.

Optionally the lipid mixture of the invention contains up to 5% by weight of neutral lipids, preferably in an amount equal to or less than 2% by weight. Neutral lipids comprise triacylglycerols, cholesterol, cholesterol esters and fatty acids such as palmitic acid.

The preferred neutral lipid is cholesterol since it may aid to reduce the viscosity of the lipid mixture.

As an example of lipid mixtures of the invention DPPC:PLPC:SAPC:DPPG:POPG in the ratio 45:30:10:5:10 (by weight) and DPPC:liver PL:POPG in the ratio 50:40:10 (by weight) have been used.

The lipid mixtures of the invention can be particularly useful in the preparation of a reconstituted surfactant.

In a particular embodiment the present invention concerns a reconstituted surfactant comprising one of previously described lipid mixtures in combination with a surfactant protein isolated from animals or manufactured through recombinant technology such as those described in WO 95/32992, or with synthetic analogues of the surfactant proteins SP-B or SP-C such as those described in WO 89/06657, WO 92/22315 and WO 00/47623 or with mixtures thereof.

The protein can be any surfactant protein, selected from SP-A, SP-B, SP-C, SP-D or a synthetic or recombinant analogue thereof.

The reconstituted surfactant of the invention can also comprise a polymyxin, preferably polymyxin B, as functional substitute of surfactant protein SP-B.

Preferably as a synthetic analogues of SP—C, a peptide of general formula (I) according to one-letter amino acid code will be utilised:

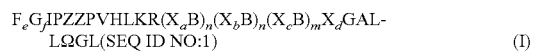

wherein:

X is an amino acid selected from the group consisting of I, L and nL (norleucine);

B is an amino acid selected from the group consisting of K, I, W, F, Y and ornithine;

Z is S optionally substituted with acyl groups containing 12-22 carbon atoms linked to the side chain via an ester bond;

Ω is an amino acid selected from the group consisting of M, I, L and nL (norleucine);

a is an integer from 1 to 19, preferably from 1 to 11;
b is an integer from 1 to 19, preferably from 1 to 8;
c is an integer from 1 to 21, preferably from 1 to 5;
d is an integer from 0 to 20, preferably from 1 to 11;
e is 0 or 1;
f is 0 or 1;
n is 0 or 1;
m is 0 or 1;

wherein, preferably:
$n+m \geq 0$;
$f \geq e$,
$(X_aB)_n(X_bB)_n(X_cB)_mX_d$ is a sequence having a maximum of 22 amino acids, preferably from 10 to 22.

Even more preferred is the use of peptides of formula (II)

wherein:

B is an amino acid selected from the group consisting of K, W, F, Y and ornithine Ω is an amino acid selected from the group consisting of M, I, L and nL (norleucine);

and wherein serine can optionally be acylated, for example with palmitoyl.

The hereinafter reported peptide (SP-C33), in the non-acylated form, is the most preferred of the invention:

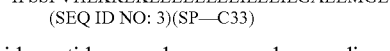

Said peptides can be prepared according to the method reported in WO 00/47623.

The amount of the surfactant protein or of the peptide in the reconstituted surfactant will vary in the range of 0.1% to 5%, preferably 0.5% to 3%, more preferably between 1% and 2% on the weight of the total mixture.

The claimed reconstituted surfactants will be prepared by mixing solutions in organic solvents of the lipid mixture with the peptide or the protein and subsequently drying the preparation until a dry powder is obtained.

The invention also concerns pharmaceutical formulations consisting of a synthetic surfactant comprising a lipid mixture of the invention for administration to subjects in need of a therapeutic treatment of surfactant deficiency.

Said pharmaceutical formulations will be administered intratracheally or by nebulisation in the form of suspensions in an aqueous medium or by aerosol administration in a suitable propellant. Preferably they will be administered intratracheally as a suspension in 0.9% sodium chloride aqueous solution. Advantageously, the surfactant concentration (expressed as phospholipid content) will be higher than 30 mg/ml, preferably higher than 40 mg/ml, more preferably higher than 50 mg/ml, even more preferably between 50 and 80 mg/ml.

At a surfactant concentration comprised between 50 and 80 mg/ml, the viscosity of the surfactant measured at 250° C. applying a shear rate ranging from 100 and 500 $s^{-1}$ will be advantageously comprised between 2 and 30 centipoise, preferably between 5 and 20 centipoise, more preferably comprised between 6 and 15 centipoise, even more preferably between 6 and 10 centipoise.

The surfactant comprising the lipid mixture of the invention can be used for the treatment of all cases of surfactant deficiencies and typically in the treatment of neonatal respiratory distress syndrome (NRDS), acute respiratory distress syndrome in adults (ARDS), meconium aspiration syndrome (MAS), several types of pneumonia and bronchopulmonary dysplasia.

The advantages of the present invention will be illustrate by the following examples.

EXAMPLE 1

Preparation of the Reconstituted Surfactants

Materials

The phospholipids 1,2-dipalmitoyl-sn-glycero-3-phosphocholine (DPPC), 1,2-dipalmitoyl-sn-glycero-3-phosphoglycerol (DPPG), 1-palmitoyl-2-oleyl-sn-glycero-3-phosphoglycerol (POPG), 1-palmitoyl-2-linoleyl-sn-glycero-3-phosphocholine (PLPC), 1-stearoyl-2-arachidonoyl-sn-glycero-3-phosphocholine (SAPC) and the phospholipid mixture obtained by isolation from liver (liver-PL) have been used for preparing the lipid mixtures and have been commercially acquired.

The peptide SP-C33 was synthesised according to the method reported in WO 00/47623.

Preparation of the Reconstituted Surfactants

The lipids, dissolved in chloroform/methanol 98:2 (v/v), were mixed in the proportions DPPC:PLPC:SAPC:DPPG: POPG and DPPC:liver PL:POPG in the ratio 45:30:10:5:10 and 50:40:10 by weight, respectively, in order to obtain lipid mixtures according to the teaching of the present invention (lipid mixtures A and B). Corresponding reconstituted surfactant preparations (surfactant A and B) were prepared by adding SP-C33 to the lipid mixture, in an amount of 2% by weight. The surfactant A was evaporated under nitrogen and resuspended in 150 mmol/l NaCl at lipid concentrations of 10 mg/ml and 80 mg/ml, respectively, while the surfactant B was resuspended at a lipid concentration of 80 mg/ml.

The phospholipid composition of the liver-PL of the surfactant B is characterised as follows: phosphatidylcholine (PC) 50%, phosphatidyletanolamine (PE) 25%, sphingomyelin (SM) 10%, acidic phospholipids 15%.

EXAMPLE 2

In Vitro Activity

Surface properties were determined in a captive bubble surfactometer. The chamber was filled with a sucrose solution and 2 μl of surfactant A (10 mg/ml) was injected; a bubble was then created insufflating 10 microliters of air. Surface tension at the air-liquid interface was determined from the shape of the bubble during film adsorption and subsequent quasi-static cyclic area compression.

Surfactant A demonstrated a good performance in term of surface area compression required to reach minimal surface tension.

EXAMPLE 3

In Vivo Activity of Surfactant A

Pre-term rabbit fetuses (n=34) were delivered at a gestational age of 27 days by caesarian section (term=31 days). At delivery, the animals were anaesthetized with intraperitoneal sodium pentobarbital (0.1 ml; 6 mg/ml), tracheotomized, paralyzed with intra-peritoneal pancuronium bromide (0.1-0.15 ml; 0.2 mg/ml) and kept in a plethysmograph system at 37° C. They were mechanically ventilated in parallel with a modified Servo-Ventilator delivering 100% oxygen. After surfactant instillation, peak pressure was first raised to 35 cmH$_2$O for 1 min, to facilitate the distribution of the surfactant in the lungs, and then lowered to 25 cmH$_2$O. The animals were then ventilated with a peak pressure of 25 cmH$_2$O for 15 min, which was lowered to 20 cmH$_2$O for 5 min, and further on to 15 cmH$_2$O for 5 min, and then raised again to 25 cmH$_2$O for 5 min. Tidal volumes were recorded at 5 min intervals by means of a pneumotachograph connected to the pletysmograph box.

The frequency was 40 per minute, the inspiration:expiration time ratio 1:1. No positive end-expiratory pressure was applied.

The immature newborn rabbits were randomized to receive at birth, via the tracheal cannula, 2.5 ml/kg body weight of surfactant A (80 mg/ml). In control animals, no material was instilled into the airways. All animals were ventilated for 30 min.

Tidal volumes ($V_T$) were measured with a plethysmograph system as described in Sun et al, *Eur Respir J* 1991, 4, 364-370 and end-expiratory lung gas volumes (LGV) were estimated from the difference between lung volume and lung wet weight (Scherle et al *Mikroscopie* 1970, 26, 57).

In these experiments it was observed that surfactant A exhibited high tidal volumes. Also the Lung Gas Volumes values were remarkably increased.

EXAMPLE 4

In Vivo Activity of Surfactant B

The surfactant B (80 mg/ml) and a commercially available modified natural surfactant (Curosurf) (80 mg/ml) were compared for tidal volume and lung gas volume in the same animal model of Example 3: the reconstituted surfactant B prepared according to the invention showed an activity comparable to that of the modified natural surfactant.

The invention claimed is:

1. A lipid mixture for preparing a synthetic surfactant, said lipid mixture comprising at least 95% by weight of phospholipids, said phospholipids comprising:
   1,2-dipalmitoyl-sn-glycero-3-phosphocholine (DPPC) in an amount of at least 40% by weight;
   polyunsaturated phospholipids in an amount higher than 10% by weight, said polyunsaturated phospholipids selected from the group consisting of 1-palmitoyl-2-linoleyl-sn-glycero-3-phosphocholine (PLPC), 1-palmitoyl-2-arachidonoyl-sn-glycero-3-phosphocholine (PAPC), 1-stearoyl-2-arachidonoyl-sn-glycero-3-phosphocholine (SAPC), phosphatidylethanolamine isolated from egg (egg-PE) and a phospholipid mixture obtained by isolation from liver (liver-PL);
   and saturated or monounsaturated acidic phospholipids in an amount higher than 10% by weight;
   wherein all the amounts are calculated on the total weight of the lipid mixture.

2. The lipid mixture according to claim 1, further comprising a neutral lipid in an amount up to 5% by weight on the total weight of the lipid mixture.

3. The lipid mixture according to claim 2, wherein the neutral lipid is selected from the group consisting of triacylglycerols, cholesterol, cholesterol esters and fatty acids.

4. The lipid mixture according to claim 1, wherein the amount of DPPC is between 40% and 65% by weight.

5. The lipid mixture according to claim 4 wherein the amount of DPPC is between 45% and 55% by weight.

6. The lipid mixture according to claim 1 wherein the amount of polyunsaturated phospholipids is higher than 20% by weight.

7. The lipid mixture according to claim 6 wherein the amount of polyunsaturated phospholipids is between 30% and 40% by weight.

8. The lipid mixture according to claim 1 wherein the amount of acidic phospholipids is between 15% and 30% by weight.

9. The lipid mixture according to claim 1, wherein the acidic phospholipids are selected from the group consisting of 1,2-dipalmitoyl-sn-glycero-3-phosphoglycerol (DPPG), 1-palmitoyl-2-oleyl-sn-glycero-3-phosphoglycerol (POPG), 1,2-dioleyl-sn-glycero-3-phosphoglycerol (DOPG), 1-palmitoyl-2-oleyl-sn-glycero-3-phosphocholine (POPC), and 1,2-dipalmitoyl-sn-glycero-3-phospho-L-serine (DPPS).

10. The lipid mixture according to claim 9, wherein the acidic phospholipids are selected from the group consisting of DPPG, POPG and their mixture.

11. The lipid mixture according to claim 1, wherein a ratio between saturated and unsaturated (monounsaturated and polyunsaturated) phospholipids is between 65:35 and 40:60 by weight.

12. The lipid mixture according to claim 1, wherein a ratio between the acidic phospholipids and the other phospholipids is between 10:90 and 30:70 by weight.

13. A reconstituted surfactant comprising the lipid mixture of claim 1 in combination with one or more surfactant proteins selected from SP-A, SP-B, SP-C, and SP-D, or their synthetic or recombinant analogues.

14. The reconstituted surfactant according to claim 13, wherein the surfactant protein is a synthetic or recombinant analogue of SP-C of general formula (I), according to the amino acids one-letter code:

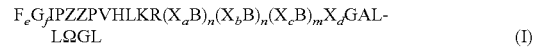

$$F_eG_fIPZZPVHLKR(X_aB)_n(X_bB)_n(X_cB)_mX_dGAL\text{-}L\Omega GL \tag{I}$$

wherein:
X is an amino acid selected from the group consisting of I, L and nL (norleucine);
B is an amino acid selected from the group consisting of K, I, W, F, Y and ornithine;
Z is S optionally substituted with acyl groups containing 12-22 carbon atoms linked to the side chain via an ester bond;
Ω is an amino acid selected from the group consisting of M, I, L, nL;
a is an integer from 1 to 19;
b is an integer from 1 to 19;
c is an integer from 1 to 21;
d is an integer from 0 to 20;
e is 0 or 1;
f is 0 or 1;
n is 0 or 1;
m is 0 or 1;

wherein n+m≧0;

f>e, and (XaB)n(XbB)n(XcB)mXd is a sequence having a maximum of 22 amino acids.

15. The reconstituted surfactant according to claim 14, wherein the SP-C analogue has the formula (II):

IPSSPVHLKRLBLLLLLLLLILLLILGALLΩGL
(SEQ ID NO: 2)     (II)

wherein

B is an amino acid selected from the group consisting of K, W, F, Y and ornithine; and Ω is an amino acid selected from the group consisting of M, I, L and nL.

16. The reconstituted surfactant according to claim 15, wherein the SP-C analogue has the following amino acid composition:

IPSSPVHLKRLKLLLLLLLLILLLILGALLMGL (SEQ ID NO: 3).

17. A pharmaceutical formulation comprising the reconstituted surfactant of claim 14.

18. The pharmaceutical formulation according to claim 17 in the form of suspension in 0.9% sodium chloride aqueous solution, wherein the reconstituted surfactant concentration (expressed as phospholipid content) is higher than 30 mg/ml.

19. The pharmaceutical formulation according to claim 18, wherein the reconstituted surfactant concentration is higher than 40 mg/ml.

20. The pharmaceutical formulation according to claim 19, wherein the reconstituted surfactant concentration is higher than 50 mg/ml.

21. The pharmaceutical formulation according to claim 20, wherein the reconstituted surfactant concentration is comprised between 50 mg/ml and 80 mg/ml.

22. The pharmaceutical formulation according to claim 17, which has a viscosity between 5 and 20 centipoise.

23. The pharmaceutical formulation according to claim 22, which has a viscosity between 6 and 15 centipoise.

24. The reconstituted surfactant of claim 14, wherein (XaB)n(XbB)n(XcB)mXd is a sequence having from 10 to 22 amino acid residues.

25. The reconstituted surfactant according to claim 13, wherein the one or more surfactant protein(s) is present in amount of about 0.1% to 5% by weight of total mixture.

* * * * *

SEQUENCE LISTING

```
<160> NUMBER OF SEQ ID NOS: 3

<210> SEQ ID NO 1
<211> LENGTH: 101
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Phe or is absent
<220> FEATURE:
<221> NAME/KEY: MISC_FEATURE
<222> LOCATION: (2)..(2)
<223> OTHER INFORMATION: Xaa = Gly or is absent
<220> FEATURE:
<221> NAME/KEY: MISC_FEATURE
<222> LOCATION: (13)..(13)
<223> OTHER INFORMATION: Xaa = Ile, Leu, Nle or is absent
<220> FEATURE:
<221> NAME/KEY: MISC_FEATURE
<222> LOCATION: (14)..(14)
<223> OTHER INFORMATION: Xaa = Ile, Leu, Nle or is absent
<220> FEATURE:
<221> NAME/KEY: MISC_FEATURE
<222> LOCATION: (15)..(15)
<223> OTHER INFORMATION: Xaa = Ile, Leu, Nle or is absent
<220> FEATURE:
<221> NAME/KEY: MISC_FEATURE
<222> LOCATION: (16)..(16)
<223> OTHER INFORMATION: Xaa = Ile, Leu, Nle or is absent
<220> FEATURE:
<221> NAME/KEY: MISC_FEATURE
<222> LOCATION: (17)..(17)
<223> OTHER INFORMATION: Xaa = Ile, Leu, Nle or is absent
<220> FEATURE:
<221> NAME/KEY: MISC_FEATURE
<222> LOCATION: (18)..(18)
<223> OTHER INFORMATION: Xaa = Ile, Leu, Nle or is absent
<220> FEATURE:
<221> NAME/KEY: MISC_FEATURE
<222> LOCATION: (19)..(19)
<223> OTHER INFORMATION: Xaa = Ile, Leu, Nle or is absent
<220> FEATURE:
<221> NAME/KEY: MISC_FEATURE
<222> LOCATION: (20)..(20)
<223> OTHER INFORMATION: Xaa = Ile, Leu, Nle or is absent
<220> FEATURE:
<221> NAME/KEY: MISC_FEATURE
<222> LOCATION: (21)..(21)
<223> OTHER INFORMATION: Xaa = Ile, Leu, Nle or is absent
<220> FEATURE:
<221> NAME/KEY: MISC_FEATURE
<222> LOCATION: (22)..(22)
<223> OTHER INFORMATION: Xaa = Ile, Leu, Nle or is absent
<220> FEATURE:
<221> NAME/KEY: MISC_FEATURE
<222> LOCATION: (23)..(23)
<223> OTHER INFORMATION: Xaa = Ile, Leu, Nle or is absent
<220> FEATURE:
<221> NAME/KEY: MISC_FEATURE
<222> LOCATION: (24)..(24)
<223> OTHER INFORMATION: Xaa = Ile, Leu, Nle or is absent
<220> FEATURE:
<221> NAME/KEY: MISC_FEATURE
<222> LOCATION: (25)..(25)
<223> OTHER INFORMATION: Xaa = Ile, Leu, Nle or is absent
<220> FEATURE:
<221> NAME/KEY: MISC_FEATURE
<222> LOCATION: (26)..(26)
<223> OTHER INFORMATION: Xaa = Ile, Leu, Nle or is absent
<220> FEATURE:
<221> NAME/KEY: MISC_FEATURE
<222> LOCATION: (27)..(27)
<223> OTHER INFORMATION: Xaa = Ile, Leu, Nle or is absent
```

-continued

```
<220> FEATURE:
<221> NAME/KEY: MISC_FEATURE
<222> LOCATION: (28)..(28)
<223> OTHER INFORMATION: Xaa = Ile, Leu, Nle or is absent
<220> FEATURE:
<221> NAME/KEY: MISC_FEATURE
<222> LOCATION: (29)..(29)
<223> OTHER INFORMATION: Xaa = Ile, Leu, Nle or is absent
<220> FEATURE:
<221> NAME/KEY: MISC_FEATURE
<222> LOCATION: (30)..(30)
<223> OTHER INFORMATION: Xaa = Ile, Leu, Nle or is absent
<220> FEATURE:
<221> NAME/KEY: MISC_FEATURE
<222> LOCATION: (31)..(31)
<223> OTHER INFORMATION: Xaa = Ile, Leu, Nle or is absent
<220> FEATURE:
<221> NAME/KEY: MISC_FEATURE
<222> LOCATION: (32)..(32)
<223> OTHER INFORMATION: Xaa = K, I, W, F, Y, Orn, or is absent
<220> FEATURE:
<221> NAME/KEY: MISC_FEATURE
<222> LOCATION: (33)..(33)
<223> OTHER INFORMATION: Xaa = Ile, Leu, Nle or is absent
<220> FEATURE:
<221> NAME/KEY: MISC_FEATURE
<222> LOCATION: (34)..(34)
<223> OTHER INFORMATION: Xaa = Ile, Leu, Nle or is absent
<220> FEATURE:
<221> NAME/KEY: MISC_FEATURE
<222> LOCATION: (35)..(35)
<223> OTHER INFORMATION: Xaa = Ile, Leu, Nle or is absent
<220> FEATURE:
<221> NAME/KEY: MISC_FEATURE
<222> LOCATION: (36)..(36)
<223> OTHER INFORMATION: Xaa = Ile, Leu, Nle or is absent
<220> FEATURE:
<221> NAME/KEY: MISC_FEATURE
<222> LOCATION: (37)..(37)
<223> OTHER INFORMATION: Xaa = Ile, Leu, Nle or is absent
<220> FEATURE:
<221> NAME/KEY: MISC_FEATURE
<222> LOCATION: (38)..(38)
<223> OTHER INFORMATION: Xaa = Ile, Leu, Nle or is absent
<220> FEATURE:
<221> NAME/KEY: MISC_FEATURE
<222> LOCATION: (39)..(39)
<223> OTHER INFORMATION: Xaa = Ile, Leu, Nle or is absent
<220> FEATURE:
<221> NAME/KEY: MISC_FEATURE
<222> LOCATION: (40)..(40)
<223> OTHER INFORMATION: Xaa = Ile, Leu, Nle or is absent
<220> FEATURE:
<221> NAME/KEY: MISC_FEATURE
<222> LOCATION: (41)..(41)
<223> OTHER INFORMATION: Xaa = Ile, Leu, Nle or is absent
<220> FEATURE:
<221> NAME/KEY: MISC_FEATURE
<222> LOCATION: (42)..(42)
<223> OTHER INFORMATION: Xaa = Ile, Leu, Nle or is absent
<220> FEATURE:
<221> NAME/KEY: MISC_FEATURE
<222> LOCATION: (43)..(43)
<223> OTHER INFORMATION: Xaa = Ile, Leu, Nle or is absent
<220> FEATURE:
<221> NAME/KEY: MISC_FEATURE
<222> LOCATION: (44)..(44)
<223> OTHER INFORMATION: Xaa = Ile, Leu, Nle or is absent
<220> FEATURE:
<221> NAME/KEY: MISC_FEATURE
<222> LOCATION: (45)..(45)
<223> OTHER INFORMATION: Xaa = Ile, Leu, Nle or is absent
<220> FEATURE:
<221> NAME/KEY: MISC_FEATURE
<222> LOCATION: (46)..(46)
<223> OTHER INFORMATION: Xaa = Ile, Leu, Nle or is absent
<220> FEATURE:
<221> NAME/KEY: MISC_FEATURE
<222> LOCATION: (47)..(47)
```

-continued

```
<223> OTHER INFORMATION: Xaa = Ile, Leu, Nle or is absent
<220> FEATURE:
<221> NAME/KEY: MISC_FEATURE
<222> LOCATION: (48)..(48)
<223> OTHER INFORMATION: Xaa = Ile, Leu, Nle or is absent
<220> FEATURE:
<221> NAME/KEY: MISC_FEATURE
<222> LOCATION: (49)..(49)
<223> OTHER INFORMATION: Xaa = Ile, Leu, Nle or is absent
<220> FEATURE:
<221> NAME/KEY: MISC_FEATURE
<222> LOCATION: (50)..(50)
<223> OTHER INFORMATION: Xaa = Ile, Leu, Nle or is absent
<220> FEATURE:
<221> NAME/KEY: MISC_FEATURE
<222> LOCATION: (51)..(51)
<223> OTHER INFORMATION: Xaa = Ile, Leu, Nle or is absent
<220> FEATURE:
<221> NAME/KEY: MISC_FEATURE
<222> LOCATION: (52)..(52)
<223> OTHER INFORMATION: Xaa = K, I, W, F, Y, Orn, or is absent
<220> FEATURE:
<221> NAME/KEY: MISC_FEATURE
<222> LOCATION: (53)..(53)
<223> OTHER INFORMATION: Xaa = Ile, Leu, Nle or is absent
<220> FEATURE:
<221> NAME/KEY: MISC_FEATURE
<222> LOCATION: (54)..(54)
<223> OTHER INFORMATION: Xaa = Ile, Leu, Nle or is absent
<220> FEATURE:
<221> NAME/KEY: MISC_FEATURE
<222> LOCATION: (55)..(55)
<223> OTHER INFORMATION: Xaa = Ile, Leu, Nle or is absent
<220> FEATURE:
<221> NAME/KEY: MISC_FEATURE
<222> LOCATION: (56)..(56)
<223> OTHER INFORMATION: Xaa = Ile, Leu, Nle or is absent
<220> FEATURE:
<221> NAME/KEY: MISC_FEATURE
<222> LOCATION: (57)..(57)
<223> OTHER INFORMATION: Xaa = Ile, Leu, Nle or is absent
<220> FEATURE:
<221> NAME/KEY: MISC_FEATURE
<222> LOCATION: (58)..(58)
<223> OTHER INFORMATION: Xaa = Ile, Leu, Nle or is absent
<220> FEATURE:
<221> NAME/KEY: MISC_FEATURE
<222> LOCATION: (59)..(59)
<223> OTHER INFORMATION: Xaa = Ile, Leu, Nle or is absent
<220> FEATURE:
<221> NAME/KEY: MISC_FEATURE
<222> LOCATION: (60)..(60)
<223> OTHER INFORMATION: Xaa = Ile, Leu, Nle or is absent
<220> FEATURE:
<221> NAME/KEY: MISC_FEATURE
<222> LOCATION: (61)..(61)
<223> OTHER INFORMATION: Xaa = Ile, Leu, Nle or is absent
<220> FEATURE:
<221> NAME/KEY: MISC_FEATURE
<222> LOCATION: (62)..(62)
<223> OTHER INFORMATION: Xaa = Ile, Leu, Nle or is absent
<220> FEATURE:
<221> NAME/KEY: MISC_FEATURE
<222> LOCATION: (63)..(63)
<223> OTHER INFORMATION: Xaa = Ile, Leu, Nle or is absent
<220> FEATURE:
<221> NAME/KEY: MISC_FEATURE
<222> LOCATION: (64)..(64)
<223> OTHER INFORMATION: Xaa = Ile, Leu, Nle or is absent
<220> FEATURE:
<221> NAME/KEY: MISC_FEATURE
<222> LOCATION: (65)..(65)
<223> OTHER INFORMATION: Xaa = Ile, Leu, Nle or is absent
<220> FEATURE:
<221> NAME/KEY: MISC_FEATURE
<222> LOCATION: (66)..(66)
<223> OTHER INFORMATION: Xaa = Ile, Leu, Nle or is absent
<220> FEATURE:
<221> NAME/KEY: MISC_FEATURE
```

-continued

```
<222> LOCATION: (67)..(67)
<223> OTHER INFORMATION: Xaa = Ile, Leu, Nle or is absent
<220> FEATURE:
<221> NAME/KEY: MISC_FEATURE
<222> LOCATION: (68)..(68)
<223> OTHER INFORMATION: Xaa = Ile, Leu, Nle or is absent
<220> FEATURE:
<221> NAME/KEY: MISC_FEATURE
<222> LOCATION: (69)..(69)
<223> OTHER INFORMATION: Xaa = Ile, Leu, Nle or is absent
<220> FEATURE:
<221> NAME/KEY: MISC_FEATURE
<222> LOCATION: (70)..(70)
<223> OTHER INFORMATION: Xaa = Ile, Leu, Nle or is absent
<220> FEATURE:
<221> NAME/KEY: MISC_FEATURE
<222> LOCATION: (71)..(71)
<223> OTHER INFORMATION: Xaa = Ile, Leu, Nle or is absent
<220> FEATURE:
<221> NAME/KEY: MISC_FEATURE
<222> LOCATION: (72)..(72)
<223> OTHER INFORMATION: Xaa = Ile, Leu, Nle or is absent
<220> FEATURE:
<221> NAME/KEY: MISC_FEATURE
<222> LOCATION: (73)..(73)
<223> OTHER INFORMATION: Xaa = Ile, Leu, Nle or is absent
<220> FEATURE:
<221> NAME/KEY: MISC_FEATURE
<222> LOCATION: (74)..(74)
<223> OTHER INFORMATION: Xaa = K, I, W, F, Y, Orn or is absent
<220> FEATURE:
<221> NAME/KEY: MISC_FEATURE
<222> LOCATION: (75)..(75)
<223> OTHER INFORMATION: Xaa = Ile, Leu, Nle or is absent
<220> FEATURE:
<221> NAME/KEY: MISC_FEATURE
<222> LOCATION: (76)..(76)
<223> OTHER INFORMATION: Xaa = Ile, Leu, Nle or is absent
<220> FEATURE:
<221> NAME/KEY: MISC_FEATURE
<222> LOCATION: (77)..(77)
<223> OTHER INFORMATION: Xaa = Ile, Leu, Nle or is absent
<220> FEATURE:
<221> NAME/KEY: MISC_FEATURE
<222> LOCATION: (78)..(78)
<223> OTHER INFORMATION: Xaa = Ile, Leu, Nle or is absent
<220> FEATURE:
<221> NAME/KEY: MISC_FEATURE
<222> LOCATION: (79)..(79)
<223> OTHER INFORMATION: Xaa = Ile, Leu, Nle or is absent
<220> FEATURE:
<221> NAME/KEY: MISC_FEATURE
<222> LOCATION: (80)..(80)
<223> OTHER INFORMATION: Xaa = Ile, Leu, Nle or is absent
<220> FEATURE:
<221> NAME/KEY: MISC_FEATURE
<222> LOCATION: (81)..(81)
<223> OTHER INFORMATION: Xaa = Ile, Leu, Nle or is absent
<220> FEATURE:
<221> NAME/KEY: MISC_FEATURE
<222> LOCATION: (82)..(82)
<223> OTHER INFORMATION: Xaa = Ile, Leu, Nle or is absent
<220> FEATURE:
<221> NAME/KEY: MISC_FEATURE
<222> LOCATION: (83)..(83)
<223> OTHER INFORMATION: Xaa = Ile, Leu, Nle or is absent
<220> FEATURE:
<221> NAME/KEY: MISC_FEATURE
<222> LOCATION: (84)..(84)
<223> OTHER INFORMATION: Xaa = Ile, Leu, Nle or is absent
<220> FEATURE:
<221> NAME/KEY: MISC_FEATURE
<222> LOCATION: (85)..(85)
<223> OTHER INFORMATION: Xaa = Ile, Leu, Nle or is absent
<220> FEATURE:
<221> NAME/KEY: MISC_FEATURE
<222> LOCATION: (86)..(86)
<223> OTHER INFORMATION: Xaa = Ile, Leu, Nle or is absent
<220> FEATURE:
```

```
<221> NAME/KEY: MISC_FEATURE
<222> LOCATION: (87)..(87)
<223> OTHER INFORMATION: Xaa = Ile, Leu, Nle or is absent
<220> FEATURE:
<221> NAME/KEY: MISC_FEATURE
<222> LOCATION: (88)..(88)
<223> OTHER INFORMATION: Xaa = Ile, Leu, Nle or is absent
<220> FEATURE:
<221> NAME/KEY: MISC_FEATURE
<222> LOCATION: (89)..(89)
<223> OTHER INFORMATION: Xaa = Ile, Leu, Nle or is absent
<220> FEATURE:
<221> NAME/KEY: MISC_FEATURE
<222> LOCATION: (90)..(90)
<223> OTHER INFORMATION: Xaa = Ile, Leu, Nle or is absent
<220> FEATURE:
<221> NAME/KEY: MISC_FEATURE
<222> LOCATION: (91)..(91)
<223> OTHER INFORMATION: Xaa = Ile, Leu, Nle or is absent
<220> FEATURE:
<221> NAME/KEY: MISC_FEATURE
<222> LOCATION: (92)..(92)
<223> OTHER INFORMATION: Xaa = Ile, Leu, Nle or is absent
<220> FEATURE:
<221> NAME/KEY: MISC_FEATURE
<222> LOCATION: (93)..(93)
<223> OTHER INFORMATION: Xaa = Ile, Leu, Nle or is absent
<220> FEATURE:
<221> NAME/KEY: MISC_FEATURE
<222> LOCATION: (94)..(94)
<223> OTHER INFORMATION: Xaa = Ile, Leu, Nle or is absent
<220> FEATURE:
<221> NAME/KEY: MISC_FEATURE
<222> LOCATION: (99)..(99)
<223> OTHER INFORMATION: Xaa = M, I, L or Nle

<400> SEQUENCE: 1

Xaa Xaa Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Gly Ala
                85                  90                  95

Leu Leu Xaa Gly Leu
            100

<210> SEQ ID NO 2
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (12)..(12)
<223> OTHER INFORMATION: Xaa = K, I, W, F, Y or Orn
<220> FEATURE:
<221> NAME/KEY: MISC_FEATURE
<222> LOCATION: (31)..(31)
<223> OTHER INFORMATION: Xaa = M, I, L or Nle

<400> SEQUENCE: 2

Ile Pro Ser Ser Pro Val His Leu Lys Arg Leu Xaa Leu Leu Leu Leu
1               5                   10                  15
```

```
Leu Leu Leu Leu Ile Leu Leu Leu Ile Leu Gly Ala Leu Leu Xaa Gly
            20                  25              30

Leu

<210> SEQ ID NO 3
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 3

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Met Gly
            20                  25              30

Leu
```